United States Patent [19]

Morita et al.

[11] Patent Number: 4,558,161

[45] Date of Patent: Dec. 10, 1985

[54] PROCESS FOR PREPARING HALO-SUBSTITUTED DIARYLSULFONES

[75] Inventors: Yukichi Morita; Koji Ono; Eiji Ogata, all of Wakayama; Osamu Manabe, Osaka, all of Japan

[73] Assignee: Konishi Chemical Industry Co., Ltd., Wakayama, Japan

[21] Appl. No.: 588,865

[22] PCT Filed: May 20, 1983

[86] PCT No.: PCT/JP83/00155

§ 371 Date: Jan. 25, 1984

§ 102(e) Date: Jan. 25, 1984

[87] PCT Pub. No.: WO83/04251

PCT Pub. Date: Dec. 8, 1983

[30] Foreign Application Priority Data

May 25, 1982 [JP] Japan ................ 57-89455

[51] Int. Cl.$^4$ ........................... C07C 147/06
[52] U.S. Cl. ........................ 568/34; 568/28; 568/33; 568/35
[58] Field of Search ........................ 568/34

[56] References Cited

U.S. PATENT DOCUMENTS

| | | | |
|---|---|---|---|
| 2,593,001 | 4/1952 | Bender et al. | 568/34 |
| 2,860,168 | 11/1958 | Erickson | 568/34 |
| 2,999,883 | 9/1961 | Schoot et al. | 568/34 |
| 3,057,925 | 10/1962 | Schoot et al. | 568/34 |
| 3,579,590 | 5/1971 | Davis | 568/34 |
| 3,632,642 | 1/1972 | Rosin et al. | 568/34 |
| 3,855,312 | 12/1974 | Horner | 568/34 |
| 4,012,451 | 3/1977 | Enoki et al. | 568/34 |

Primary Examiner—Donald G. Daus
Assistant Examiner—S. A. Gibson
Attorney, Agent, or Firm—Armstrong, Nikaido, Marmelstein & Kubovcik

[57] ABSTRACT

A process for preparing diarylsulfone, the process comprising reacting chlorosulfonic acid with a mixture of (i) aromatic hydrocarbon represented by the formula

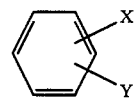

wherein one of X and Y is a halogen atom and the other is a halogen atom or a hydrogen atom and (ii) aromatic sulfonic acid represented by the formula

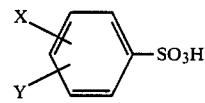

wherein X and Y are as defined above.

5 Claims, No Drawings

PROCESS FOR PREPARING HALO-SUBSTITUTED DIARYLSULFONES

TECHNICAL FIELD

This invention relates to an improved process for preparing diarylsulfones or more specifically, diarylsulfones having halogen on the aromatic ring, such as 4,4'-dichlorodiphenylsulfone and the like.

Diarylsulfones are industrially useful compounds as intermediates for synthesizing pharmaceuticals, dyes and the like or as materials for preparing various types of synthetic resins, epoxy resin-curing agents, etc.

A variety of processes as given below are known for producing diarylsulfones.

(1) A process in which benzene, chlorobenzene, toluene or like aromatic hydrocarbon is reacted with a mixture of sulfuric anhydride and dimethyl pyrosulfate (Japanese Pat. Nos. 301684; 305463; and 312809).

(2) A process in which aromatic hydrocarbon such as those mentioned above and p-toluenesulfochloride, p-chlorobenzenesulfochloride or like aromatic sulfochloride are subjected to Friedel-Crafts reaction in the presence of anhydrous iron chloride, anhydrous aluminum chloride or the like (German Pat. No. 701954).

(3) A process in which aromatic hydrocarbon such as those exemplified above is reacted with aromatic sulfochloride such as above in the presence of benzenesulfonic acid, 4-chlorobenzenesulfonic acid, or like aromatic sulfonic acid (Japanese Examined Patent Publication No. 5707/1975).

(4) A process in which aromatic hydrocarbon such as above and aromatic sulfonic acid such as above are subjected to condensation reaction using phosphorus pentoxide or like phosphorus oxide-type dehydrating agent (Japanese Examined Patent Publication No. 24662/1968).

(5) A process in which reaction is conducted between aromatic hydrocarbon such as above and aromatic sulfonic acid such as above at a high temperature of more than 200° C. (Japanese Unexamined Patent Publication No. 76834/1974 and U.S. Pat. No. 2593001).

(6) A process in which specific amounts of halobenzene compound and chlorosulfonic acid are subjected to reaction at less than 10° C. and thereafter a specific amount of halobenzene compound is further added to the resulting reaction mixture, followed by heating of the mixture at 40° to 60° C. (U.S. Pat. No. 2860168).

However, all of these processes have drawbacks to be remedied and remain unsatisfactory from commercial viewpoints. More specifically stated, the process (1) uses dimethyl sulfate having high toxicity and thus is impractical because of the problems on operators' sanitation and disposal of waste water. The processes (2) and (3) employ aromatic sulfochloride as the starting material which is difficult to obtain and which is prone to hydrolysis in handling and during storage, requires reaction at a high temperature of more than 100° C. and gives product with low purities. The process (4) entails reaction which continues over a period of about 24 hours at a high temperature of over 80° C., usually 130° to 180° C. and results in the production of a product with low purities. The process (5) requires reaction at a high temperature of more than 200° C. and produces a product having low purities in low yields. The process (6) needs a low-temperature reaction, provides a product, although with high purities, in yields as low as about 30%, necessitates a cooling device to maintain the reaction system at a low temperature of less than 10° C., usually −5° to 5° C. and involves a cumbersome procedure due to the two-step reaction. In short, these conventional processes suffer from the disadvantages with respect to starting materials to be used, procedures involved, reaction efficiency, equipment, etc. and generally entail reaction at high temperatures, fail to give a desired product with high purities in high yields and require purification of the reaction product using a solvent or the like to obtain a commercially acceptable end product.

DISCLOSURE OF THE INVENTION

An object of the present invention is to provide an improved process for preparing diarylsulfones, the process giving a desired product with high purities in high yields, using inexpensive and readily available starting materials and involving a simple procedure to be easily carried out at a mild temperature in the vicinity of room temperature and completed in a short period of time without entailing a step or device for heating or cooling.

More specifically stated, the present invention provides a process for preparing diarylsulfone, the process comprising reacting chlorosulfonic acid with a mixture of (i) aromatic hydrocarbon represented by the formula

(I)

wherein one of X and Y is a halogen atom and the other is a halogen atom or a hydrogen atom and (ii) aromatic sulfonic acid represented by the formula

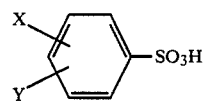

(II)

wherein X and Y are as defined above.

According to the present invention, desired diarylsulfones can be produced efficiently with considerably high purities in significantly high yields by conducting a simplified, single-step reaction under mild conditions for a short period of time without using aromatic sulfochlorides which are difficult to obtain and which require special care in handling and during storage, dimethyl sulfate of high toxicity and the like. The reaction in accordance with the present invention rapidly proceeds at ordinary temperatures and pressures, without using a device for heating and cooling the reaction system, and produces a desired product with such high purities (over 99.5%) that the product thus prepared can be used with effectiveness for various purposes without being purified, subsequent to the reaction. Therefore, this invention is particularly suited to industrial application.

Specific examples of the aromatic hydrocarbons represented by the formula (I) and to be used as the starting material in the present invention are chlorobenzene, bromobenzene, fluorobenzene, iodobenzene, dichlorobenzene, dibromobenzene, etc. Preferred examples of useful aromatic sulfonic acids represented by the formula (II) are chlorobenzenesulfonic acid, bromobenzenesulfonic acid, dichlorobenzenesulfonic acid and the like which each correspond to the above-mentioned aromatic hydrocarbons. It is generally desired to use aromatic sulfonic acids in the form of anhydride.

The present invention can be practiced usually by preparing a mixture of the aromatic hydrocarbon and the aromatic sulfonic acid and adding chlorosulfonic acid to the mixture for reaction. The aromatic sulfonic acid is mixed with the aromatic hydrocarbon in an amount of usually about 0.3 to about 2 moles, preferably about 0.8 to about 1.2 moles, per mole of the former. If the aromatic sulfonic acid is present in an amount far smaller than the range, diarylsulfone is produced in reduced yields. The use of the acid in excess of the foregoing range is likely to provide an end product in decreased yields rather than increased yields. An appropriate amount of chlorosulfonic acid to be used ranges usually from about 0.8 to about 1.5 moles per mole of the aromatic hydrocarbon. The yield and the purity of diarylsulfone produced is affected by the amount of chlorosulfonic acid used. Below the range, reduced yields result, whereas above the range, no yield is enhanced but purity is lowered due to production of a by-product in a larger amount.

The reaction according to the present invention favorably proceeds by maintaining the reaction system at a temperature of less than 60° C., usually about 10° to about 30° C. With the reaction at more than 60° C., the yield of diarylsulfone obtained tends not to increase, rather decreasing as compared with the reaction at less than 60° C., although with the result of the aromatic hydrocarbon observed as consumed. The reaction at extremely low temperature entails a cooling device or the like and is caused to continue for a prolonged period of time. According to the present invention, the reaction is completed when the evolution of hydrochloric acid gas has ceased, usually several hours after the start of addition of chlorosulfonic acid. After the completion of the reaction, water is added to the reaction mixture and, when required, the unreacted aromatic hydrocarbon is separated and recovered by distillation or like method, whereby diarylsulfone can be obtained as a precipitate. From the filtrate left after the separation of the precipitate can be recovered a portion of aromatic sulfonic acid which can be reused for the ensuing reaction of the present invention.

The diarylsulfone thus obtained generally has a considerably high purity of about more than 99.5% (according to liquid chromatography) and thus can be used for various purposes without being purified. But the product may be purified, of course, by conventional purifying procedure.

The present invention will be described below in more detail with reference to the following examples and comparison example.

EXAMPLE 1

A 211 g (1.1 moles) quantity of 4-chlorobenzenesulfonic acid was added to 112 g (1 mole) of chlorobenzene and the mixture was cooled with water while 123 g (1.1 moles) of chlorosulfonic acid was added to the mixture at about 10° to about 20° C. over a period of 1 hour. After the addition, the reaction mixture was stirred for 3 hours while being maintained at 20° to 30° C. The hydrochloric acid gas evolved during the reaction was continuously removed from the reaction system. After the termination of the reaction, about 400 ml of water was added to the reaction mixture and 11.2 g (0.1 mole) of the unreacted chlorobenzene was recovered by distillation. The separation of the precipitate formed gave 77 g of 4,4'-dichlorodiphenylsulfone in a yield of 60% (based on the amount of the aromatic hydrocarbon as consumed, the same hereinafter). M.P. 148.5° to 149.5° C. Purity of 99.8% (according to liquid chromatography, the same hereinafter).

COMPARISON EXAMPLE 1

To 112 g (1 mole) of chlorobenzene was added 123 g (1.1 moles) of chlorosulfonic acid at 10° to 20° C. After the addition, while being maintained at 20° to 30° C., the mixture was stirred for 3 hours to complete the reaction. A 0.1 mole quantity of the unreacted chlorobenzene was recovered in the same manner as in Example 1 and 32 g of 4,4'-dichlorodiphenylsulfone was obtained in 25% yield. M.P. 148.5° to 149.5° C. Purity of 99.8%.

EXAMPLE 2

The same procedure as in Example 1 was repeated by using 147 g (1 mole) of o-dichlorobenzene, 250 g (1.1 moles) of 1,2-dichlorobenzene-4-sulfonic acid and 174 g (1.5 moles) of chlorosulfonic acid and recovering 14.7 g (0.1 mole) of the unreacted o-dichlorobenzene, whereby 85 g of 3,3', 4,4'-tetrachlorodiphenylsulfone was given in 53% yield. M.P. 176.5° to 177.5° C. Purity of 99.9%.

EXAMPLE 3

The procedure of Example 1 was followed with the exception of altering the amount of 4-chlorobenzenesulfonic acid used to 96 g (0.5 mole), giving 58 g of 4,4'-dichlorodiphenylsulfone in 45% yield. M.P. 148.5° to 149.5° C. Purity of 99.8%.

EXAMPLE 4

A 194 g (1.1 moles) quantity of 4-fluorobenzenesulfonic acid was added to 96 g (1 mole) of fluorobenzene and the mixture was cooled with water while 123 g (1.1 moles) of chlorosulfonic acid was added at about 10° to about 20° C. over a period of 1 hour. After the addition, the reaction mixture was stirred for 3 hours while being maintained at 20° to 30° C. The hydrochloric acid gas evolved during the reaction was continuously removed from the reaction system. After the completion of the reaction, about 400 ml of water was added to the reaction mixture, and 9.6 g (0.1 mole) of the unreacted fluorobenzene was recovered by distillation. Separation of the precipitate by filtration gave 65 g of 4,4'-difluorodiphenylsulfone in 58% yield. M.P. 97° to 98° C. Purity of 99.7%.

EXAMPLE 5

To 204 g (1 mole) of iodobenzene was added 312 g (1.1 moles) of 4-iodobenzenesulfonic acid and the mixture was cooled with water while 123 g of (1.1 moles) of chlorosulfonic acid was added thereto at about 10° to about 20° C. over a period of 1 hour. After the addition, the reaction system was stirred for 3 hours while being maintained at 20° to 30° C. The hydrochloric acid gas evolved during the reaction was continuously removed from the reaction system. After the completion of the reaction, about 400 ml of water was added to the reaction mixture and 20 g of (0.1 mole) of the unreacted iodobenzene was was recovered by distillation. Separation of the precipitate by filtration gave 123 g of 4,4'-diiododiphenylsulfone in 58% yield. M.P. 201° to 202° C. Purity of 99.6%.

We claim:

1. A process for preparing a diarylsulfone, the process comprising reacting chlorosulfonic acid with a mixture of (i) a halogenated aromatic hydrocarbon represented by the formula

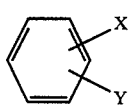 (I)

wherein one of X and Y is a halogen atom and the other is a halogen atom or a hydrogen atom and (ii) a halogenated aromatic sulfonic acid corresponding to said halogenated aromatic hydrocarbon (i) and represented by the formula

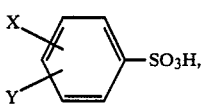 (II)

wherein X and Y are identical to X and Y of said halogenated aromatic hydrocarbon (i).

2. A process as defined in claim 1 in which the halogenated aromatic hydrocarbon is selected from the group consisting of chlorobenzene, bromobenzene, fluorobenzene, iodobenzene, dichlorobenzene and dibromobenzene and the halogenated aromatic sulfonic acid is the correspondingly halogenated aromatic sulfonic acid.

3. A process as defined in claim 1 in which the mixture of the halogenated aromatic hydrocarbon and the halogenated aromatic sulfonic acid comprises about 0.8 to about 1.2 moles of the latter per mole of the former.

4. A process as defined in claim 1 in which the chlorosulfonic acid is used in an amount of about 0.8 to about 1.5 moles per mole of the halogenated aromatic hydrocarbon.

5. A process as defined in claim 1 in which the reaction is conducted at a temperature of 10° to 60° C.

* * * * *